United States Patent [19]

Ackermann et al.

[11] 4,079,058
[45] Mar. 14, 1978

[54] PROCESS OF PERFORMING CYCLIZATION REACTIONS USING BENZYL OR PYRIDYLAMINO MALONIC ACID DERIVATIVES

[75] Inventors: Otto Ackermann, Troisdorf-Sieglar; Karl-Theo von Meszoly, Troisdorf; Arnold Lenz, Cologne-Stammheim, all of Germany

[73] Assignee: Dynamit Nobel AG, Troisdorf Bezirk Cologne, Germany

[21] Appl. No.: 728,812

[22] Filed: Oct. 1, 1976

Related U.S. Application Data

[63] Continuation of Ser. No. 499,965, Aug. 23, 1974, abandoned.

[30] Foreign Application Priority Data

Aug. 29, 1973   Germany .............................. 2343462

[51] Int. Cl.$^2$ .................. C07D 215/56; C07D 471/04
[52] U.S. Cl. ...................... 260/283 SY; 260/287 AN; 260/295 N
[58] Field of Search ................. 260/287 AN, 283 SY, 260/295 N

[56] References Cited

U.S. PATENT DOCUMENTS 3,761,482   9/1973   Nakagome et al. .......... 260/287 AN

OTHER PUBLICATIONS

Lappin, "J. Am. Chem. Soc." 70, (1948), 3348.

*Primary Examiner*—Donald G. Daus
*Assistant Examiner*—David E. Wheeler
*Attorney, Agent, or Firm*—Burgess, Dinklage & Sprung

[57] ABSTRACT

Process of producing a naphthyridine or quinoline compound of the formula:

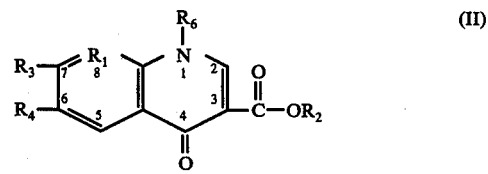

wherein $R_2$, $R_3$, $R_4$, and $R_6$ can be alkyl, and $R_1$ is nitrogen or CH. The corresponding pyridyl- or phenylaminomethylenemalonic acid diester is cyclized to yield said compound and an alcohol. The malonic acid diester at below reaction temperature is added to a solvent, e.g., diphenyl benzene, at above reaction temperature in proportion so that the mixture attains reaction temperature. Good yields at high throughputs are achieved.

23 Claims, No Drawings

PROCESS OF PERFORMING CYCLIZATION REACTIONS USING BENZYL OR PYRIDYLAMINO MALONIC ACID DERIVATIVES

This is a continuation, of application Ser. No. 499,965, filed Aug. 23, 1974 now abandoned.

BACKGROUND

The invention relates to a generally practicable method of performing cyclization reactions with the yielding of a submolecule, which take place only at relatively high temperatures above those which can be achieved with conventional solvents.

The method is especially suitable for those cyclization reactions in which an alcohol is split off from an ester group of the starting substance.

Such reactions have hitherto been conducted but incompletely, because at the high temperature at which the splitting off of the alcohol group and the cyclization reactions take place numerous secondary and competing reactions diminish the yeild and contaminate the desired product. It is known, for example, that in the cyclization of 2-pyridylaminomethylenemalonic acid esters with the removal of alcohol, 1,8-naphthyridine derivatives are formed. According to R. Lappin, J. Am. Chem. Soc. 70 (1948), 3348, however, 7-methyl-4-hydroxy-3-carbethoxynaphthyridine 1,8 is obtained in a good yield only if the methylpyridylaminomethylenemalonic acid diethyl ester is fed to a refluxing solution of diphenyl ether at about 260° C and the reaction solution is chilled as quickly as possible after a reaction time of 10 minutes. In this process small amounts around approximately 0.1 mole produce good yields, whereas Lappin obtains "much smaller yields without exception" from larger batches. Our own experiments resulted, despite rapid chilling, in a reduction of the yield to 45 to 55% of the theory as soon as the input was increased above about 20 grams.

THE INVENTION

The subject of the invention is a method of performing cyclization reactions in high-boiling solvents in the temperature range from 200° C to 360° C with the splitting off of a submolecule and cooling of the reaction mixture, which is characterized in that the starting compound, melted or dissolved in a suitable high-boiling solvent, is heated and mixed with a larger amount of the high-boiling solvent heated to 240° C to 360° C, the cyclization is performed at the resulting intermediate temperature of 200° to 350° C, and then the reaction mixture is cooled, and the product is then obtained from the solvents.

This process is surprisingly suitable for producing on a technical scale regularly high yields of at least 80%, usually of as mich as 97%, of the cyclizates of the starting compounds, it being possible and preferable to perform it continuously with precisely maintained detention times which may amount to a few minutes to about half an hour.

For the achievement of such excellent yields and for the prevention of side reactions, a certain narrowly limited reaction time must be adhered to in the cyclization, which depends, within certain limits, on the cyclization temperature and on the apparatus used in the performance of the cyclization.

It is important to prevent back-mixing, so that every amount of the substance will always be in the apparatus for the reaction time which has been found to be optimum.

Especially important in the prevention of side reaction is rapid heating, which is achieved by heating a prepared solution of the starting compound in the high-boiling solvent to a temperature at which neither the cyclization reaction nor any side reactions take place, and then pouring this solution into a generally larger amount of the high-boiling solvent heated to a temperature higher than the cyclization temperature.

The cyclization temperature, which will depend on the temperature difference between the solution and the hotter solvent and on their quantities, may amount in general to from 200° to 350° C, preferably 240° to 330° C.

The temperature of the previously prepared solution of the starting compound will generally be 100° to 200° C below the cyclization temperature selected, preferably 140° to 160° C below the cyclization temperature. Preferably the temperature of said prepared solution of starting compounds will be between 130° and 200° C. The quantity ratio of the solution to the hotter high-boiling solvent may vary slightly depending on the difference between the temperature of the solution and the cyclization temperature. In general, however, the high-boiling solvent will be used in a quantity amounting to 2 to 12 times, and preferably 5 to 10 times, the quantity of the solution of the starting material.

The high-boiling solvents must have a boiling point at or above the cyclization temperature but must not participate in the reaction or decompose to any great extent even after long use and after recovery.

Suitable solvents are generally high-boiling aromatic, especially multinuclear aromatic hydrocarbons, such as diphenylbenzene, dibenzylbenzene or ditolyl, and in some cases araliphatic hydrocarbons such as diphenylethane, triphenylmethane or tetraphenylmethane, and in some cases ketones of the aromatic series such as benzophenone or aliphatic or aromatic carboxylic acid esters such as, for example, terephthalic acid dimethyl ester, or fatty acid glycerol or polyclycerol esters.

The reaction may be performed in one or in a plurality of reaction vessels connected in series. If only one reaction vessel is present, the operation will be performed in batches, the solution of the starting substance being poured into the vessel containing the pre-heated high-boiling solvents, and the chilling being performed after a period of agitation and reaction. In general, agitation by intense stirring with a high-speed stirrer of great efficiency is advantageous. When a plurality of reactors is used they may be in the form of vats, the first serving as a mixing vessel, the reaction mixture being transformed every few minutes from one vat to the next, while being agitated in the first or perferably in all of the reactors, and being discharged from the last reactor for chilling. In the vessels provided with agitation the preferred speed of the stirrer is 50 to 300 and occasionally as much as 1000 revolutions per minute.

It is desirable to provide the reaction vessel or vessels with a condenser, a system for temperature measurement, valves through which starting solution and solvents may be put in, and a discharge valve, and to control its temperature by means of a heating system and a cooling system.

The continuous process is more desirable for the production of larger quantities on account of the short reaction time it involves, and it is preferred. The design of the reactor should be adapted to the predetermined optimum cyclization time.

In general, the detention time, and hence the cyclization time, is given, and the reaction is controlled by the choice of the cyclization temperature through the establishment of an appropriate mixture temperature through the ratio of the quantity of the heated feed solution to the quantity of the hotter solvent, the latter being the greater of the two quantities. The reaction time can be 5 – 30, preferably 10 – 20 minutes.

The chilling of the reaction solution through an abrupt and drastic temperature reduction may be performed by means of relatively low-boiling, inert liquids such as ketones, esters, especially hydrocarbons, preferably aliphatic or in some cases aromatic hydrocarbons having 6 to 10 carbon atoms.

The amount of inert cooling liquids will generally be from one to five times that of the reaction mixture.

The cooling may be further intensified by the evaporation of these liquids.

It may furthermore be desirable to pass the reaction mixture through a heat exchanger for rapid chilling. The reaction mixture diluted with the liquids is processed and filtered or centrifuged in a conventional manner after cooling.

The concentration of the solvents will generally result in the production from the mother liquid of an additional, likewise pure fraction of the product.

Due to the great difference in the boiling points of the solvents they can easily be separated by distillation and reused.

The process described, which is for reactions performable at at temperatures of 200° to 360° C, is especially suitable for the production of multinuclear heterocyclic rings containing one or more nitrogen atoms, such as the 4-hydroxy-3-carbalkoxynaphthyridines or -quinolines bearing additional substituents or not additionally substituted, setting out from the correspondingly substituted or unsubstituted pyridyl or phenylaminomethylenemalonic ester, respectively.

These additional substituents may occur in any still unoccupied positions on the rings and may be of any desired nature, as long as they are unable to react in the cyclization.

Preferred as such additional substituents, therefore, are alkyl groups and alkoxy groups, especially those with 1 to 4 carbon atoms, aromatic radicals, e.g. mononuclear aryl radicals, especially phenyl radicals, halogen atoms, especially chlorine atoms, phenolic hydroxy groups, alkyl substituents containing in some cases alcohol, keto or other groups, etc.

Further subject matter of the invention is therefore a method of performing cyclization reactions by the above-described process, which is characterized in that naphthyridines or quinolines hearing a hydroxy group in position 4 and a carbalkoxy group in position 3, and substituted or unsubstituted in other ring positions, are prepared by thermal cyclization in high-boiling solvents from correspondingly substituted or unsubstituted pyridyl- or phenylaminomethylenemalonic acid esters with the yielding of one mole of alkanol.

The alkoxy group originating from the malonic acid alkyl ester may be any one desired, but the carbomethoxy, carbethoxy and carbopropoxy groups are preferred.

During the reaction one of the two alkyl ester groups is split off in the form of the free alcohol.

For the preparation of the naphthyridine and quinoline derivatives, temperatures of 250° to 310° C and reaction times of about 8 to 15 minutes and especially about 10 minutes have proven to be especially desirable.

At temperatures below 250° C the reaction takes longer and increasingly larger amounts of undesired by-products are formed, which have to be removed by subsequent recrystallization. At temperatures above 330° C, at somewhat shorter reaction times, by-products also form, which diminish the yield.

It is possible to perform the cyclization of the naphthyridine derivatives and quinoline derivatives continuously or discontinuously.

In the preparation of the naphthyridine or quinoline derivatives it is desirable to mix the molten starting substance, or a solution, heated at 120° to 150° C, in the high-boiling solvent, with 10 to 17 times the amount of the high-boiling solvents heated to about 280° to 340° C.

The derivatives of naphthyridine and quinoline as is known constitute foreproducts for the preparation of hair dyes, for example.

Thus, the invention provides a process for cyclization of a starting compound which undergoes cyclization in liquid phase in high-boiling solvent to produce the cyclized product and a submolecule at 200°–360° C. The process comprises heating the starting material in liquid phase to a reaction temperature of 200°–350° C and maintaining it at said reaction temperature for a time period sufficient for the cyclization and insufficient for substantial side reaction, and at the end of said time period, cooling the reaction mixture to below the temperature at which said reaction and side reactions substantially occur. The starting compound is heated to said reaction temperature. Thus the starting compound in liquid phase at a temperature below the reaction temperature is mixed with a larger quantity (weight basis) of a solvent for the reaction in liquid phase at a temperature above the reaction temperature.

The reaction temperature can be the resultant temperature of the mixing, i.e. the temperature of the mixture resulting from the mixing, without any additions or subtractions of heat by an external means.

The starting compound can be a pyridyl- or phenylaminomethylenemalonic acid diester:

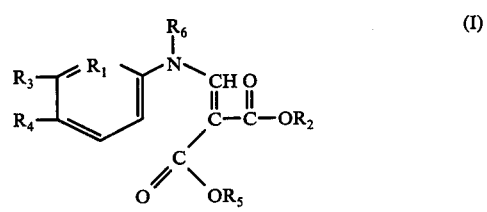

wherein:
$R_1$ is nitrogen or CH;
$R_2$ and $R_5$ is alkyl;
$R_3$ and $R_4$ is each hydrogen alkyl, alkoxy, or halogen or both together forming the bridging group
—O—CH$_2$—O— and
$R_6$ is H or alkyl
and the cyclized product is the corresponding naphthyridine or or quinoline of the formula:

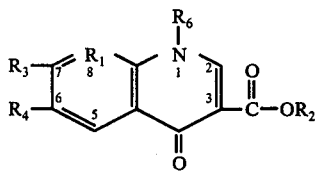

In case of $R_6=H$ there exists a tautomeric form whereby this H exists in a OH group instead of above noted oxo group (=O) in position 4* and correspondingly the relative compounds are named as 4-hydroxy compounds wherein $R_1$, $R_2$, $R_3$, $R_4$ and $R_6$ is each as in (I), and the submolecule is $R_5OH$, wherein $R_5$ is as above.

* under formal shift of the double bonds $R_2$, $R_5$ and $R_6$ can each be a alkyl of 1–4 carbon atoms and $R_3$ and $R_4$ can each be alkyl of 1–4 carbon atoms, alkoxy of 1–4 carbon atoms, or chlorine, or both together forming the brindging group —O—CH$_2$—O— thus constituting a further five atom ring inclusive the C-atoms where to $R_3$ and $R_4$ are attached, which is stable under crylisation conditions and being the ring

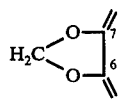

in the corresponding reaction product. $R_2$ and $R_5$ can be methyl, ethyl, or propyl.

Desirably, said solvent for the reaction is a multinuclear organic compound.

The starting compounds and the preparation thereof are known in the art.

EXAMPLE 1

Discontinuous preparation of 7-methyl-4-hydroxy-3-carbethoxy-naphthyridine-1,8.

A reaction vat with a capacity of 250 liters is charged with 150 kg of dibenzylbenzene and heated with stirring to about 330° C. Over a period of about 0.5 to 1 minute, a solution, heated to 120°–150° C, of 10 kg of methyl-pyridylaminomethylenemalonic acid diethyl ester (PMME) in 25 kg of dibenzylbenzene was added to the dibenzyl benzene. During the course of the reaction ethanol is distilled from the reaction mixture. The cyclization is terminated in 10 minutes at 300° C. The reaction solution is rapidly passed through a heat exchanger into a cooling tank filled with hexane, the considerable heat being removed both by external cooling and by evaporative cooling. The cyclizate which crystallizes is centrifuged, the filter cake is repeatedly washed with hexane, and the wash liquid is combined with the filtrate. The hexane is separated from this solution by distillation.

The mother liquor remaining in the sump of the distillation column is repeatedly fed back to the next batch before it has to be freed of by-products.

The yield of the product amounts to 92% of the theory with respect to the PMME.

EXAMPLE 2

Continuous preparation of 7-methyl-4-hydroxy-3-carbethoxy-naphthyridine-1,8.

The continuous production is performed in a tubular reactor with a capacity of 80 liters. 300 liters of dibenzylbenzene per hour are heated to 330° C, and then fed continuously to the reactor mixed with a solution of 20 kg PMME in 50 kg dibenzylbenzene heated to 150° C. The temperature of the reaction mixture is maintained at 300° C. After a reaction time of about 10 minutes the reaction product is continuously withdrawn, cooled in a heat exchanger, and diluted with approximately 1000 liters of hexane per hour. After the cooling process the cyclizate that has crystallized is removed with a centrifuge and processed as described in Example 1. An average of approximately 15.4 kg of the above-named product could be produced per hour. This corresponds to a yield of 93% of the theory with reference to PMME.

EXAMPLE 3

Discontinuous preparation of 3-carbethoxy-4-hydroxy-7-chloro-1-quinoline.

In a 250 liter vat, 150 liters of dibenzylbenzene are heated with stirring to 300° C. Over a period of 1 minute a solution of 15 kg of M-chlorophenylaminomethylenemalonic acid diethyl ester in 25 liters of dibenzyl benzene, heated to 150° C, is delivered into the hot dibenzylbenzene. The ethanol formed in the reaction distills out immediately. The reaction is terminated after about 10 to 12 minutes. Then the reaction solution is rapidly cooled and the precipitated cyclizate is removed by filtration. The filter cake is washed repeatedly with hexane and then dried. The processing of the filtrate and wash liquid is performed as described in Example 1. The yield of 3-carbethoxy-4-hydroxy-7-chloro-1-quinoline amounts to 95% of the theory, with reference to m-chlorophenylaminomethylenemalonic acid diethyl ester.

EXAMPLE 4

3-Carbethoxy-4-hydroxy-quinoline 150 liters of dibenzylbenzene are heated to about 320° C in a mixing vat with a capacity of 250 liters. With intense stirring, a solution, heated to 150° C, of 13.2 kg of anilinomethylenemalonic acid diethyl ester in 25 kg of dibenzylbenzene is added over a period of 1 to 2 minutes. The ethanol that forms distills out immediately. After about 10 minutes the reaction is ended. The reaction solution is rapidly cooled, whereupon the cyclizate crystallizes out of the still warm solution. Filtration, washing and processing of the filtrate are performed as described in Example 1.

9.9 kg of 3-carbethoxy-4-hydroxyquinoline (91% yield) were obtained.

EXAMPLE 5

3-Carbethoxy-4-hydroxy-6,7-dimethoxyquinoline 150 liters of dibenzylbenzene are heated to about 300° C in a mixing vat with a 250 liter capacity. With intense stirring, a solution, heated at 150° C of 12.5 kg of 3,4-dimethoxy-anilinomethylenemalonic acid diethyl ester in 25 kg of dibenzylbenzene, is added over a period of 1 to 2 minutes. The ethanol that forms distills out immediately. After about 12 minutes the reaction is ended. The reaction solution is rapidly cooled, the cyclizate crystallizing out of the still warm solution. Filtration, washing and processing of the filtrate are performed as described in Example 3.

10 kg of 3-carbethoxy-4-hydroxy-6,7-dimethoxyquinoline (93.5% yield) were obtained.

EXAMPLE 6

3-carbethoxy-4-hydroxy-6,7-methylenedioxy-quinoline 75 liters of dibenzylbenzene are heated to about 300° C in a mixing vat with a 150 liter capacity. With intense stirring, a solution, heated to 150° C of 6.0 kg of 3,4-methylenedioxyanilinomethylenemalonic acid diethyl ester in 12 kg of dibenzylbenzene, is added over a period of 1 to 2 minutes. The ethanol that forms distills out immediately. After about 12 to 18 minutes the reaction is ended. The reaction solution is rapidly cooled, the cyclizate crystallizing out of the still warm solution. Filtration, washing and processing of the filtrate are performed as described in Example 5.

4.8 kg of 3-carbethoxy-4-hydroxy-6,7-methylenedioxy-quinoline (95.0 yiled) were obtained, in which product the 3,4 methylenedioxy group together with the C-atoms attached to form the ring

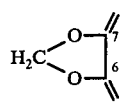 (III)

In corresponding manner N-ethyl-3,4-methylenedioxy-anilinomethylenemalonic acid diethyl ester can be converted into N-ethyl-3-carbethoxy-4-oxo-6,7-methylenedioxy-quinoline.

What is claimed is:

1. In the process of cyclization of a substituted malonic acid diester which is a pyridyl- or phenylaminomethylene malonic acid diester of the formula

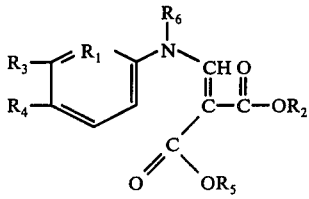 (I)

wherein:
$R_1$ is nitrogen or CH;
$R_2$ and $R_5$ is each alkyl;
$R_3$ and $R_4$ is each hydrogen, alkyl, alkoxy, or halogen, or both together form the briding group —O—CH$_2$—O—;
and $R_6$ is H or alkyl
to produce as the cyclized product the corresponding naphthyridine or quinoline of the formula:

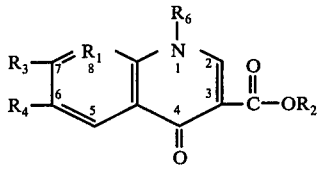 (II)

wherein $R_1$, $R_2$, $R_3$, $R_4$ and $R_6$ is each as in (I) with the splitting off of an alkoxy group and formation therefrom of an alcohol of the formula $R_5$OH wherein $R_5$ is as above, in liquid phase in high boiling solvent at 200°–360° C, comprising the steps of heating the substituted malonic acid diester in liquid phase to said temperature and maintaining it at said temperature for a reaction time sufficient for the cyclization and insufficient for substantial side reactions, and cooling the reaction mixture to below the temperature at which said reaction and side reactions substantially occur, the improvement which comprises the steps of performing the cyclization at a reaction temperature of 200°–350° C, and, for heating the substituted malonic acid diester to said reaction temperature, the substituted malonic acid diester in liquid phase, melted or in solution in a solvent at a temperature of 130°–200° C, is mixed with a quantity of a solvent for the reaction in liquid phase at a temperature above said reaction temperature and of 240°–360° C, the amount of said solvent at 240°–360° C being 2–17 times the amount of said melted substituted malonic acid diester at 130°–200° C or the amount of said solution of substituted malonic acid diester at 130°–200° C.

2. Process according to claim 1, wherein said mixing is effected by pouring the substituted malonic acid diester in liquid phase, into the solvent.

3. Process according to claim 1, wherein said reaction temperature is the resultant temperature of said mixing.

4. Process according to claim 1, wherein said liquid phase of the substituted malonic acid diester is in solution in a solvent.

5. Process according to claim 1, wherein the cyclized product is recovered from the cooled reaction mixture.

6. Process according to claim 1, wherein the cyclization is carried out in a tubular reactor.

7. Process according to claim 1, wherein said reaction temperature is controlled by adding heat to the reaction mixture.

8. Process according to claim 1, wherein said reaction temperature is controlled by removing heat from the reaction mixture.

9. Process according to claim 1, wherein said cooling is effected by passing the reaction mixture through a heat exchanger.

10. Process according to claim 1, wherein said cooling is effected by mixing a solvent at a temperature below said reaction temperature with the reaction mixture.

11. Process according to claim 10, wherein the reaction mixture is poured into said solvent at a temperature below said reaction temperature.

12. Process according to claim 10, where said solvent at a temperature below said reaction temperature is an ether, ketone, ester, or aliphatic or aromatic hydrocarbon with 6 to 10 carbon atoms.

13. Process according to claim 1, wherein $R_2$ and $R_5$ is each an alkyl of 1–4 carbon atoms, $R_3$ and $R_4$ is each alkyl of 1–4 carbon atoms, alkoxy of 1–4 carbon atoms, or chlorine and $R_6$, in the meaning alkyl, is an alkyl of 1–4 carbon atoms.

14. Process according to claim 1, wherein $R_2$, $R_5$ and $R_6$ is each methyl, ethyl, or propyl.

15. Process according to claim 1, wherein the cyclized product is:
   7-methyl-4-hydroxy-3-carbethoxy-naphthyridine-1,8
   3-carbethoxy-4-hydroxy-7-chloro-1-quinoline
   3-carbethoxy-4-hydroxy-quinoline
   3-carbethoxy-4-hydroxy-6,7-dimethoxyquinoline
   3-carbethoxy-4-hydroxy-6,7-methylenedioxy-quinoline or
   N-ethyl-3-carbethoxy-4-oxo-6,7-methylenedioxy-quinoline
and the starting compound is the corresponding pyridyl or phenylaminomethylenemalonic acid diester.

16. Process according to claim 1, wherein said solvent with which the substituted malonic acid diester is mixed in diphenylbenzene, dibenzylbenzene, or ditolyl.

17. Process of claim 1, wherein the solvent with which the substituted malonic acid diester is mixed in at 240° to 360° C.

18. Process of claim 1, wherein the reaction temperature is 250°–310° C, and the solvent with which the substituted malonic acid diester is mixed at 280°–340° C.

19. Process of claim 18, wherein the reaction time is 8–15 minutes.

20. Process of claim 1, wherein the amount of substituted malonic acid diesters is above about 20 grams.

21. Process of claim 17, wherein the reaction time is 8–15 minutes, and the amount of substituted malonic acid diester is above 20 grams.

22. Process according to claim 1, wherein the reaction time at said 200°–350° C is a few minutes to about half an hour, and the temperature of said melted substituted malonic acid diester or said solution of substituted malonic acid diester is 100°–200° C below said reaction temperature.

23. Process according to claim 22, wherein said solvent for the reaction is dibenzylbenzene and said time period is 8–15 minutes and said reaction temperature is 250°–310° C.

* * * * *

UNITED STATES PATENT AND TRADEMARK OFFICE
CERTIFICATE OF CORRECTION

PATENT NO. : 4 079 058
DATED : March 14, 1978
INVENTOR(S) : Otto Ackermann, Karl-Theo von Meszoly and Arnold Lenz It is certified that error appears in the above-identified patent and that said Letters Patent are hereby corrected as shown below:

Column 7, line 47, change "briding" to --bridging--.

Column 9, line 3, change "in" to --is--.

Signed and Sealed this

Fourth Day of July 1978

[SEAL]

Attest:

RUTH C. MASON
Attesting Officer

DONALD W. BANNER
Commissioner of Patents and Trademarks